United States Patent [19]

Ducharme et al.

[11] Patent Number: 5,000,740
[45] Date of Patent: Mar. 19, 1991

[54] CATHETER WITH NEEDLE GUARD

[75] Inventors: Leonard C. Ducharme; Joseph J. Chang, both of Tampa; Richard M. Bloom, Palm Harbor, all of Fla.

[73] Assignee: Critikon, Inc., Tampa, Fla.

[21] Appl. No.: 335,472

[22] Filed: Apr. 10, 1989

[51] Int. Cl.⁵ .............................................. A61M 5/32
[52] U.S. Cl. .................................... 604/162; 604/168; 604/198
[58] Field of Search ............... 604/162, 192, 198, 263, 604/168, 900, 158, 164–168

[56] References Cited

U.S. PATENT DOCUMENTS

| | | |
|---|---|---|
| 4,160,450 | 7/1979 | Doherty . |
| 4,500,312 | 2/1985 | McFarlane . |
| 4,631,057 | 12/1986 | Mitchell . |
| 4,655,751 | 4/1987 | Harbaugh ............................. 604/198 |
| 4,676,783 | 6/1987 | Jagger et al. . |
| 4,681,567 | 7/1987 | Masters et al. ....................... 604/198 |
| 4,702,738 | 10/1987 | Spencer . |
| 4,738,663 | 4/1988 | Bogan ................................... 604/198 |
| 4,762,516 | 8/1988 | Luther et al. . |
| 4,832,696 | 5/1989 | Luther et al. ........................ 604/168 |
| 4,838,871 | 6/1984 | Luther ................................. 604/192 |
| 4,840,619 | 6/1989 | Hughes ................................ 604/192 |
| 4,867,172 | 9/1989 | Haber et al. ......................... 604/192 |
| 4,894,055 | 1/1990 | Sudnak ................................ 604/198 |
| 4,900,310 | 2/1990 | Ogle, II ............................... 604/263 |
| 4,900,311 | 2/1990 | Stern et al. .......................... 604/263 |
| 4,950,252 | 8/1990 | Luther et al. ........................ 604/198 |

*Primary Examiner*—C. Fred Rosenbaum
*Assistant Examiner*—Kathleen A. Daley
*Attorney, Agent, or Firm*—Paul A. Coletti

[57] ABSTRACT

A catheter device is described with a safety needle guard that covers and protects the needle after use of the device. The device includes a semi-tubular needle housing containing a flash chamber with a hollow needle extending from the distal end of the flash chamber. A tubular needle guard concentrically fits and slides within the needle housing. The needle guard has a longitudinal slot through which the mounting base of the flash chamber passes as the guard slides within the housing. The top of the semi-tubular housing is open so that a user may access the top of the tubular needle guard with a finger to urge the needle guard to an extended position from the distal end of the housing and in a surrounding position about the needle. As the needle guard attains its fully extended position about the needle, it locks in place in the needle housing.

13 Claims, 7 Drawing Sheets

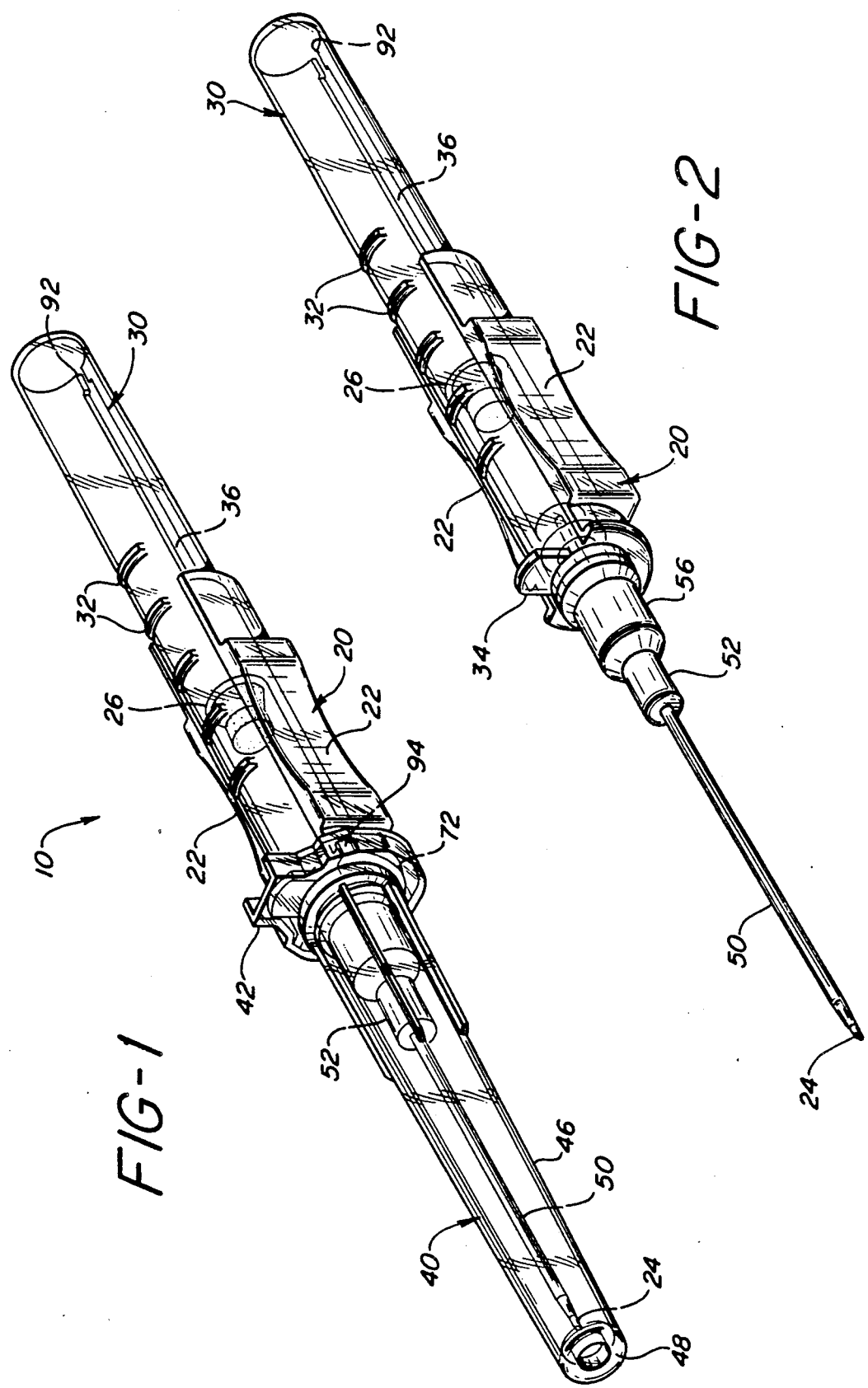

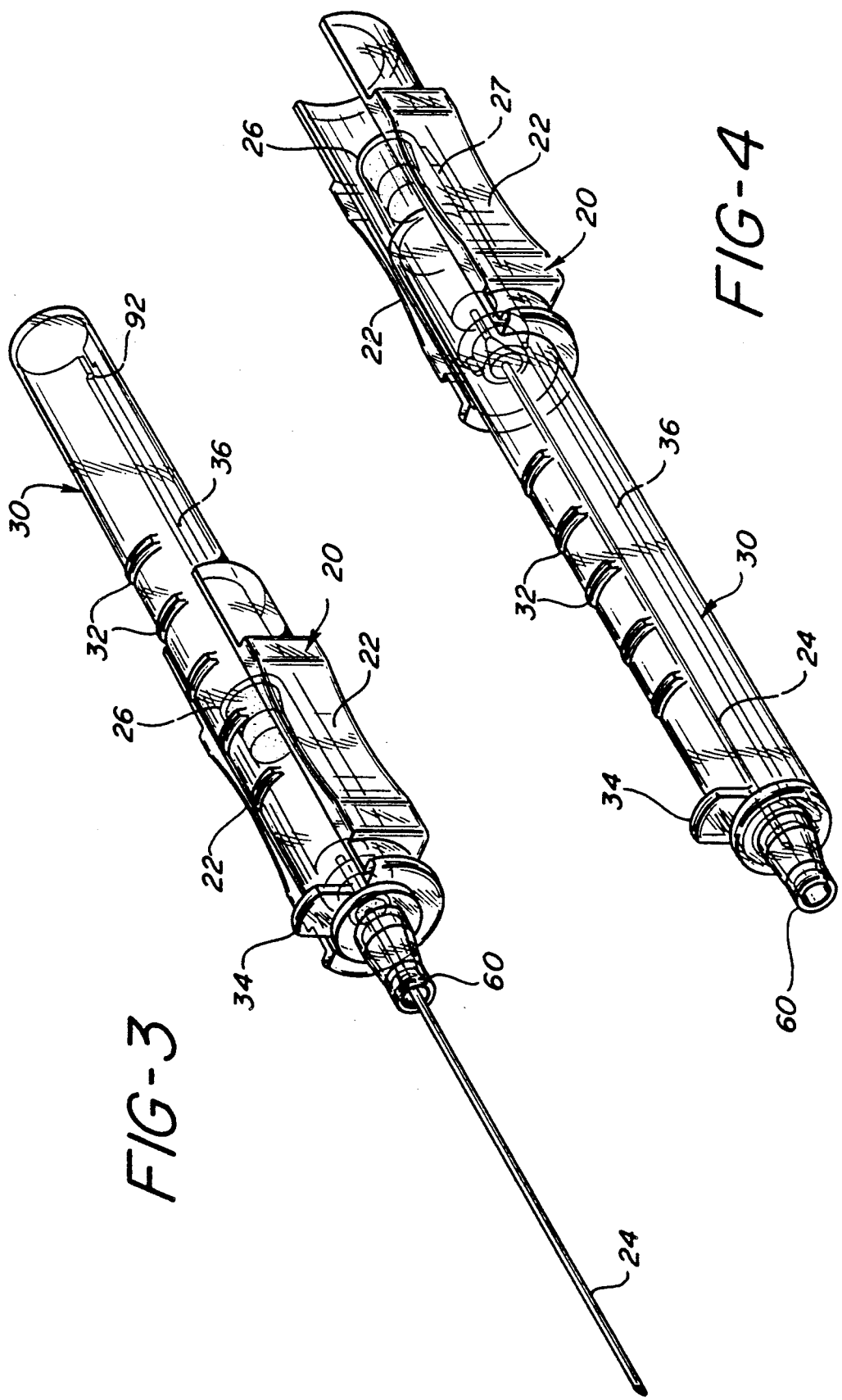

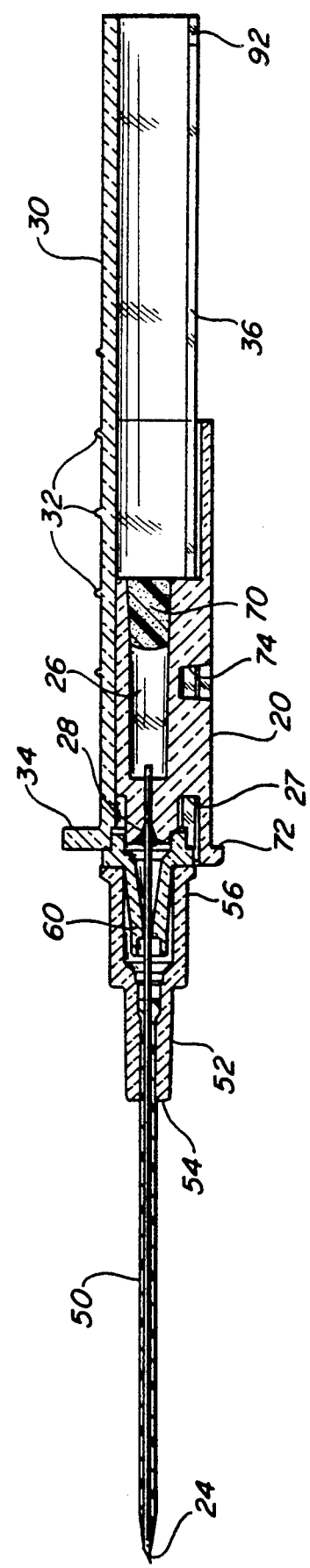

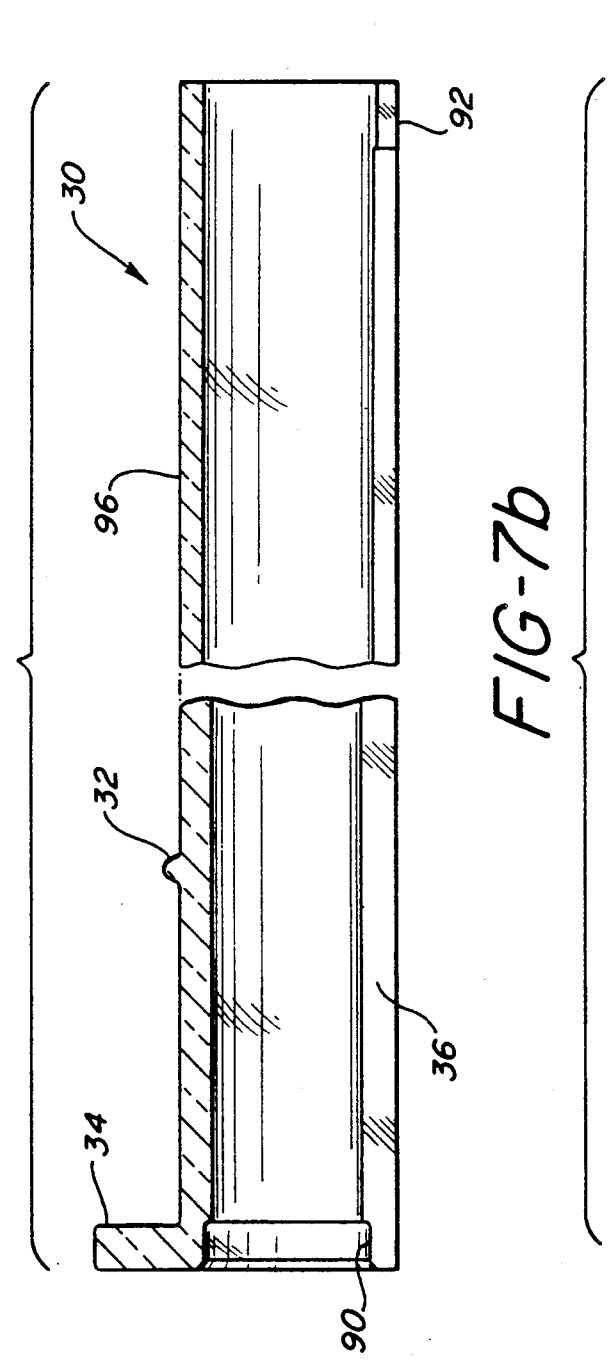
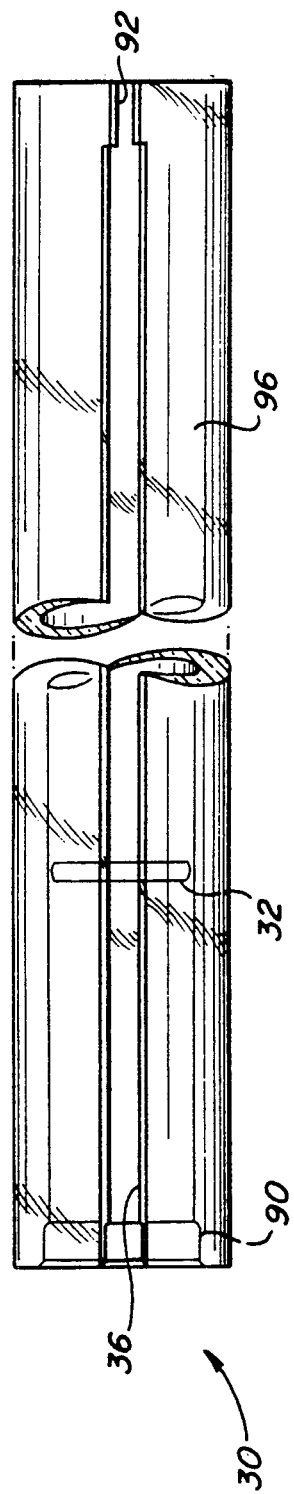
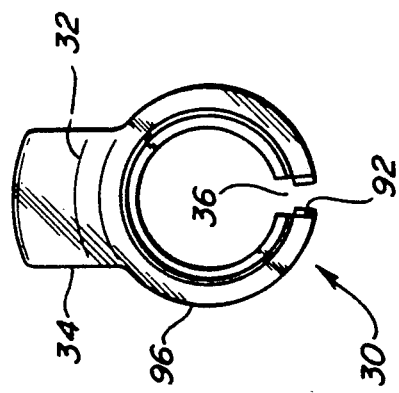

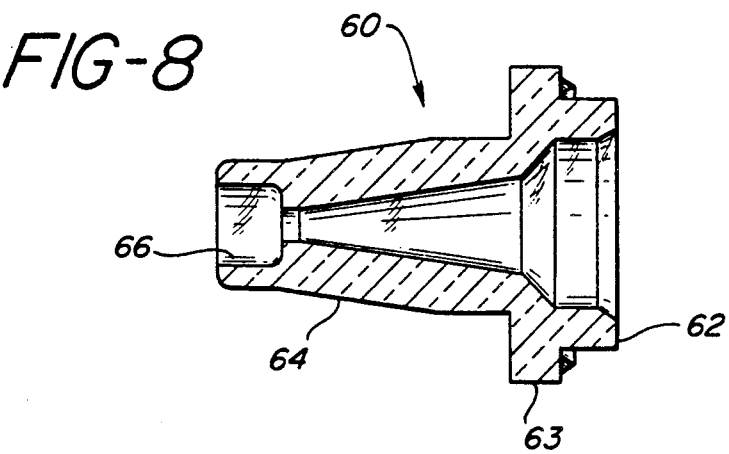
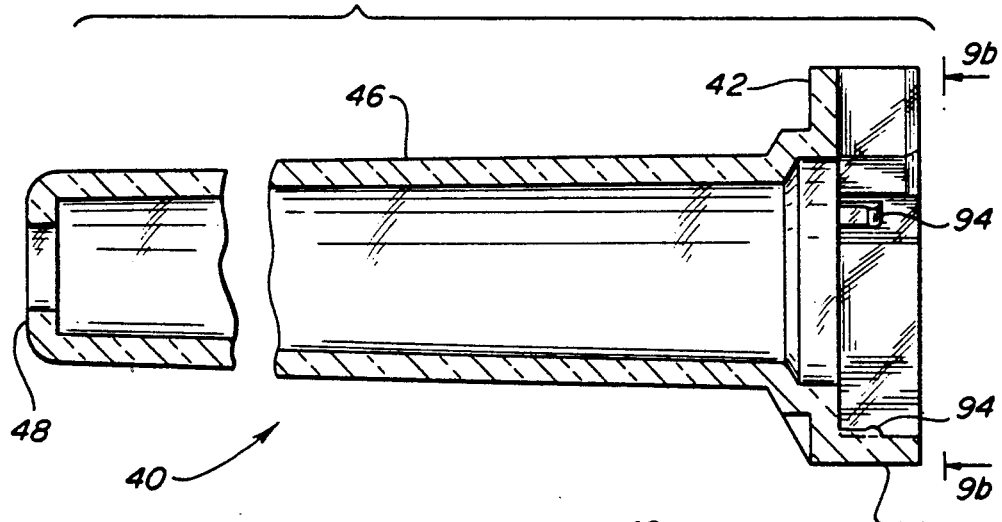
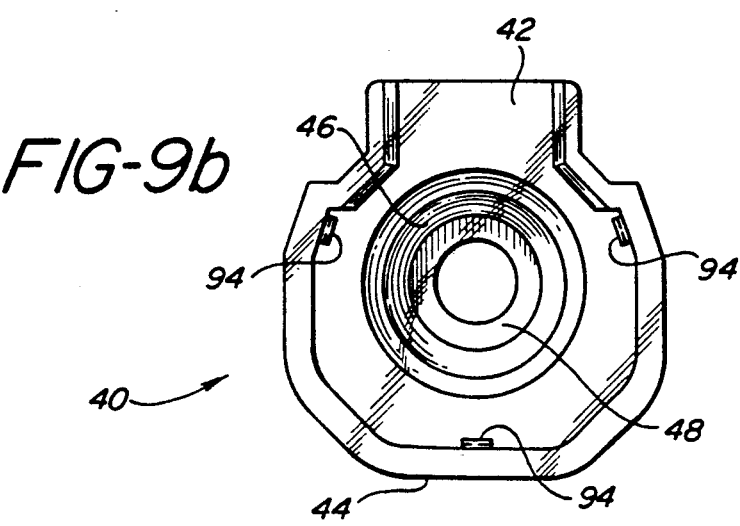

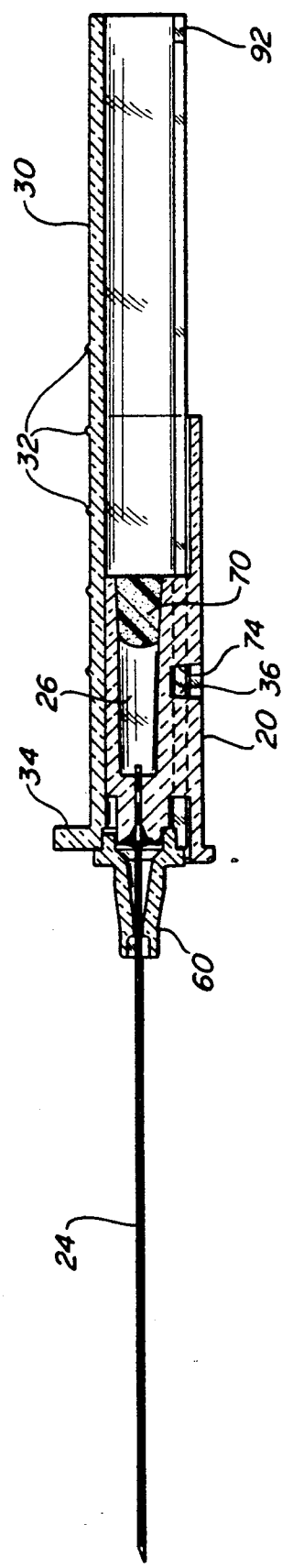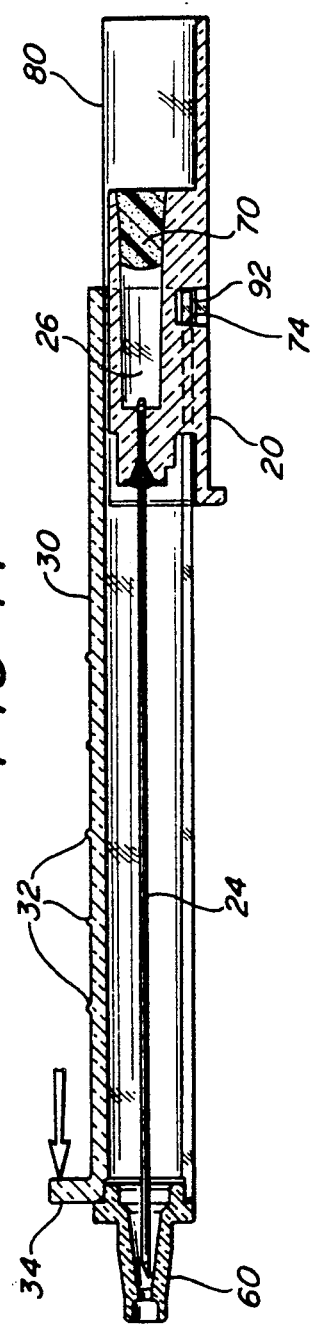

CATHETER WITH NEEDLE GUARD

This invention relates to intravascular (I.V.) catheters and, in particular, to I.V. catheter assemblies which cover the needle point after use to prevent accidental injury from used needles.

Intravenous catheters for the infusion of fluids into the peripheral veins of a patient are one of the most common devices used in I.V. therapy. I.V. catheters may be produced in two general forms: through-the-needle catheters, in which a catheter is threaded through the needle cannula and into the vein of a patient, and over-the-needle catheters, in which the needle and concentric outer catheter are inserted into the vein and the needle is withdrawn through the emplaced catheter.

A typical over-the-needle I.V. catheter assembly requires the user to remove and then dispose of a contaminated needle after the needle tip and catheter are properly located in a blood vessel of a patient. Once the needle is withdrawn from the catheter, the user's immediate priorities are infusion set connection and site preparation, including the taping of the catheter to the patient. Because of the urgency of these procedures, the needle is normally just dropped conveniently nearby and then retrieved later. Since the needle at this time is exposed and located close to where the user is completing work with the catheter, accidental self-inflicted needle injuries are not uncommon. For reasons of the desirability of protecting the user from exposure to blood borne disease such as hepatitis and AIDS, there is an increasing need to protect the user from accidental needle injury.

A catheter design which is directed toward this need is shown in U.S. Pat. No. 4,762,516. The catheter shown in this application includes an elongate body which houses a sliding needle guard. In use, the needle with its surrounding catheter tube is inserted through the skin of a patient until the tip of the needle is located in a blood vessel, a position detected by a small flow of blood through the needle and into the flash chamber of the catheter. The user then advances a tab on the top of the needle guard to simultaneously thread the catheter tube into the blood vessel and begin the retraction of the needle from the catheter tube. As the needle is withdrawn from the emplaced catheter, the advance of the tab slides the needle guard out of the housing and along the needle, until the distal end of the guard covers the needle tip and the proximal end of the guard locks in the elongate body. The needle and guard may then be set aside with the needle tip fully protected.

While the arrangement described in this patent application can provide full Protection against accidental needle injury, it would be desirable to provide such a catheter in a smaller, smoothly operating configuration which can be readily manipulated by small hands. In accordance with the principles of the present invention, a catheter assembly with needle guard is provided with a semi-tubular needle housing that is open on the upper surface. Located within the housing is a flash chamber with a needle extending from the distal end of the chamber and beyond the distal end of the housing. A tubular needle guard is located for distal movement within the semi-tubular needle housing, and has a distal opening through which the needle extends. The bottom of the needle guard is slotted to fit around the base of the flash chamber. At the rear of the needle guard slot is a portion of a locking mechanism which will engage with and lock in the needle housing when the needle guard is extended to cover the needle.

In a preferred embodiment of the present invention the needle guard includes a separate tip piece which enables the mounting of a catheter hub over the needle guard tip. The use of a separate tip also facilitates automated assembly without damage to the sharp pointed needle. When the needle guard is extended, the distal end of the tip piece extends beyond the point of the needle. The needle housing of the preferred embodiment also includes an integral, contoured finger grip located on each side of the needle housing. The catheter assemblY is further provided with a protective sheath to protect the catheter and needle prior to use.

In the drawings:

FIG. 1 is persPective view of a catheter assembly constructed in accordance with the principles of the present invention with the sheath in place;

FIG. 2 is a perspective view of the catheter assembly of FIG. 1 after removal of the sheath;

FIG. 3 is a perspective view of the needle housing, needle, and needle guard of the catheter assembly of FIG. 2 with the catheter removed;

FIG. 4 is a perspective view of the assembly of FIG. 3 with the needle guard extended;

FIG. 5 is a cross-sectional view of the catheter assembly of FIG. 2;

Figure 6A:
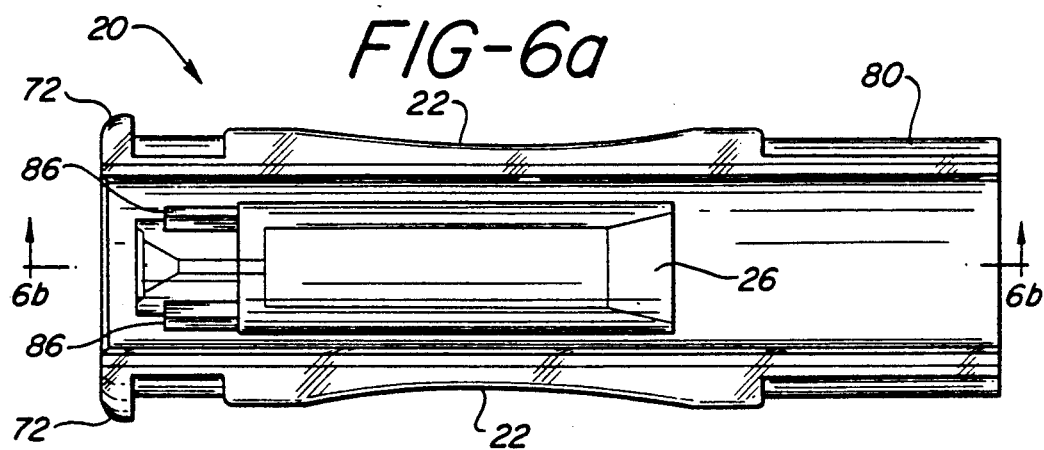
Figure 6B:
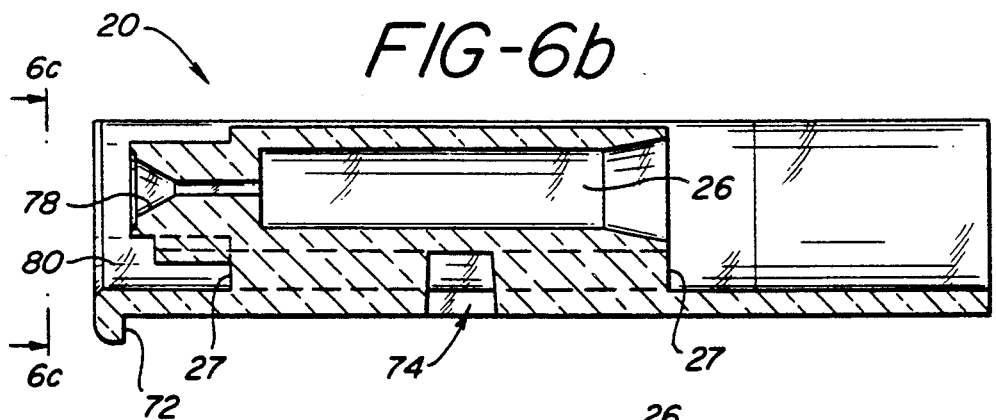

FIGS. 6a, 6b, 6c, and 6d are views of the needle housing of a catheter assembly of the present invention;

FIGS. 7a, 7b, and 7c are views of a needle guard suitable for use with the needle housing of FIGS. 6a–6d;

FIG. 8 is a cross-sectional view of a needle guard tip suitable for use with the needle guard of FIGS. 7a–7c;

FIGS. 9a and 9b are views of a sheath suitable for use with the assembly of FIG. 1;

FIG. 10 is a cross-sectional view of the needle housing and needle guard of FIGS. 6a–6d, 7a–7c and 8 with the needle guard retracted; and FIG. 11 is a cross-sectional view of the needle housing and needle guard of FIGS. 6a–6d, 7a–7c and 8 with the needle guard extended.

Referring first to FIG. 1, a catheter assembly 10 constructed in accordance with the principles of the present invention is shown. The assembly 10 includes a needle housing 20 which is semi-tubular in shape and open at the top. Molded on the sides of the needle housing 20 are opposing contoured finger grips 22, one of which is visible in FIG. 1. Located inside the semi-tubular needle housing and extending proximally therefrom is a tubular needle guard 30. On the upper surface of the needle guard are a number of small projections 32 which provide surfaces against which a user may press to fully extend the needle guard. These projections permit a user to extend the needle guard with the index or other finger while holding the catheter assembly with one hand. Extending distally from the needle housing 20 is a protective sheath 40 which covers the distally extending needle and catheter.

FIG. 2 illustrates the assembly of FIG. 1 after removal of the sheath 40. This drawing shows the catheter 50 and its catheter hub 52 mounted on the distal end of the needle guard 30. The point of the needle 24 is seen to extend from the distal tip of the catheter 50. A push-off tab 34 is seen projecting upward from the needle guard proximal the catheter hub 52.

FIG. 3 shows the assembly of FIG. 2 prior to mounting the catheter and hub on the distal end of the needle guard. Located on the distal end of the needle guard is a needle guard tip 60, through which the needle 24 extends. FIG. 4 shows the assembly of FIG. 3 after the needle guard 30 has been extended to cover the needle 24. In this position the needle guard is locked in its extended position inside the needle housing, and the point of the needle is located inside of the needle guard tip 60.

FIG. 5 is a cross-sectional view of the catheter assembly of FIG. 2. The catheter 50 is seen to extend from the distal end 54 of the catheter hub 52 and is concentric therewith. The catheter may be attached to its hub by any means known in the art, including adhesively or mechanically by means of a metal eyelet. The larger diameter proximal portion 56 of the catheter hub 52 is flanged at its proximal end for connection to an infusion set, and the inner diameter of the proximal portion of the hub is sized to fit over the distal portion of the needle guard tip 60.

The needle 24 is attached to the distal end of the flash chamber 26 of the needle housing with the proximal end of the needle terminating within the chamber. The needle 24 is affixed in place by adhesive 28. The needle extends through the needle guard tip 60, the needle hub 52, and the catheter 50, with the point of the needle extending from the distal end of the catheter. The rear of the flash chamber 26 is plugged by a microporous plug 70. The needle guard is seen to extend proximal the rear of the needle housing with the needle guard tip 60 affixed to the distal end of the needle guard at the location of the push-off tab 34. The tubular needle guard surrounds the flash chamber 26, with the base 27 of the flash chamber being located in a longitudinal slot 36 at the bottom of the needle guard. As the needle guard slides in the distal direction to cover the needle it is maintained concentric with the needle housing by the concentric tubular construction of the needle housing and needle guard and by the tracking of the base 27 of the flash chamber in the needle guard slot 36.

The needle housing of a catheter assembly constructed in accordance with the present invention is shown in FIGS. 6a, 6b, 6c, and 6d. In the top view of FIG. 6a the contoured finger grips 22 are seen on either side of the housing. A flange 72 is formed at the distal end of the housing. The flash chamber 26 is seen to be centrally located in the housing. In the cross-sectional view of FIG. 6b the distal section of the flash chamber to which the needle is attached is seen to extend beyond the base 27 of the flash chamber. The distal opening 78 for the needle 24 is flared, and this flared space is filled with adhesive to attach the needle to the flash chamber. Three ribs 86 are formed uniformly around the distal end of the flash chamber to afford more uniform material flow during the molding process. The proximal opening 76 of the flash chamber is slightly flared to permit ease of insertion of the porous flash plug 70. A rectangular aperture 74 is formed in the base of the housing below the flash chamber 26, and extends upward into the base 27 of the flash chamber.

Figure 6C:
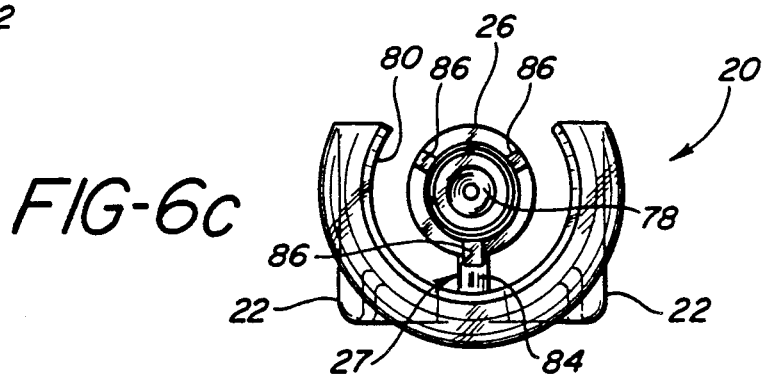

The distal end view of the needle housing of FIG. 6c shows the semi-tubular shape of the body 80 of the housing which accommodates mating with the tubular needle guard. The flash chamber 26 is seen in the center of the body extending upward from its base 27. The finger grips 22 are also seen on either side of the housing body.

Figure 6D:
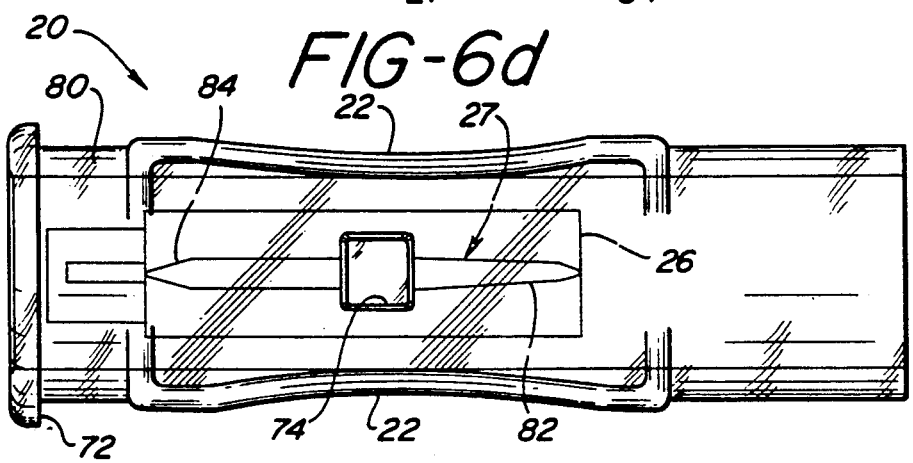

FIG. 6d is a bottom plan view of the needle housing, showing the aperture 74 formed in the bottom of the housing. Shown in phantom proximal and distal the aperture is the flash chamber base 27. As the phantom lines 82 indicate, the section of the base 27 proximal the aperture 74 is tapered from a rounded point to a greater width at the aperture 74. As explained below this tapered base and the aperture form a part of the locking mechanism for the needle guard of the catheter assembly. The distal section 84 of the base is also tapered for ease of assembly of the needle guard and housing.

A needle guard suitable for use with the needle housing of FIGS. 6a-6d is shown in FIGS. 7a, 7b, and 7c. FIG. 7a illustrates the tubular needle guard 30 with its distal push-off tab 34 and upper projections 32. The distal end 90 of the central opening of the tube is formed to accommodate insertion of the needle guard tip 60, to be discussed below. FIG. 7b is a view of the bottom of the needle guard, with its longitudinal slot 36. The slot 36 is narrowed at its proximal end 92 to form a part of the needle guard locking mechanism. FIG. 7c is a distal end view of the needle guard 30 which shows the tubular form of the guard. The outer surface 96 of the tubular structure slides smoothly inside the semi-tubular structure 80 of the needle housing of FIG. 6a-6d.

A needle guard tip 60 suitable for use with the needle guard of FIG. 7a-7c is shown in cross-section in FIG. 8. The proximal end 62 of the tip 60 is sized to fit in the distal opening 90 of the needle guard 30. The proximal end of the tip is inserted into the needle guard until the shoulder 63 of the tip contacts the distal end of the guard. The central section 64 of the tip 60 is tapered on both its internal and external surfaces. The distal end 66 of the tip 60 is rounded and open for passage of the needle through the tip.

A protective sheath 40 suitable for use with the needle housing of FIG. 6a-6d is shown in FIGS. 9a and 9b. The sheath releasably attaches to the distal end of the needle housing and is of a sufficient length to cover the catheter and needle. The body 46 of the sheath is slightly tapered from the distal end 48 of the sheath to the flange 44 at the Proximal end 44. At the top of the flange 44 is a release tab 42, used to release the sheath from the catheter assembly prior to use of the catheter. The internal diameter of the flange 44 is sized to fit over the distal flange 72 of the needle housing. Three projections 94 are formed in the inner surface of the flange 44 as shown in FIG. 9b which provide secure connection of the sheath 40 on the housing flange 72. FIG. 9b also shows that the outer periphery of the sheath is formed as a series of flat surfaces interconnected by smaller radial surfaces to retard rolling of the catheter assembly.

FIG. 10 shows the subassembly of the needle 24, the needle housing 20, the needle guard 30, the porous flash plug 70, and the needle guard tip 60. Assembly may be accomplished by inserting the flash plug 70 into the proximal end of the flash chamber 26. The needle 24 is inserted into the distal end of the flash chamber and is adhesively secured in place. With the needle and housing oriented vertically, the needle guard 30 is dropped over the needle. The large internal opening of the needle guard minimizes the Possibility of contact between the needle guard and the point of the needle, which is important to prevent damage to the sharp needle point during assembly. The needle guard then slides into the needle housing from the distal end of the housing. The tapered distal end 84 of the flash chamber base engages the proximal end of the guard slot 36 to guide the needle guard into the housing around the base 27 of the flash chamber. The guard and housing will slide together until the narrowed proximal end 92 of the slot engages the aperture 74 of the housing, causing the two components to lock together. An instrument is inserted into the aperture 74 and into slot 36 to spread the narrowed portion 92 of the slot and thereby permit the needle guard to proceed fully into the needle housing.

However, the concentric tubular construction of the needle guard and housing also permits the needle guard to slide into the housing from the proximal end of the housing. This is Preferable to the distal entry technique described above, for the catheter device can then be assembled without causing the needle guard to pass through its locking position, thereby obviating the need to unlock the narrowed portion 92 of the guard slot during assembly of the device.

With the distal end of the needle guard extending beyond the distal end of the housing, the needle guard tip 60 is dropped over the point of the needle. The small tip can be accurately aligned with its central passageway in line with the needle so that the guard tip can be slipped over the needle without damaging the point of the needle. When the proximal end 62 of the guard tip fully engages the distal opening 90 of the needle guard these two components are ultrasonically welded together. This two-component needle guard thus permits assembly of the catheter device without damage to the needle. The needle guard and tip then slide fully into the needle housing as shown in FIG. 10. The catheter 50 and hub 52 are then slipped over the needle 24 until the catheter hub 52 is securely seated over the tapered surface 64 of the needle guard tip, as shown in FIG. 5. The protective sheath may then be slipped over the catheter and needle and snapped onto the needle housing flange 72. The catheter assembly is then packaged for delivery to a user.

The catheter assembly of FIG. 5 may be used in the conventional manner by inserting the concentric catheter and needle through the skin of a patient and into a blood vessel. When the point of the needle 24 is properly located in the vessel, a small amount of blood will flow through the needle and into the flash chamber 26. Since the needle housing and guard are made of transparent or translucent polymeric materials, the flow of blood will be readily apparent in the flash chamber. The needle is then retracted from the vessel and the catheter 50 threaded into the vessel by grasping the finger grips 22 of the housing with the thumb and fingers and pushing the push-off tab 34 in the distal direction with one finger. This motion will push the catheter hub 52 off of the needle guard tip 60 to advance the catheter. As the needle guard begins to extend out from the distal end of the needle housing such that the push-off tab 34 is beyond the reach of the finger of the user, the user may engage the projections 32 with the finger to continue the distal motion of the needle guard.

Finally this motion will result in proper threading of the catheter into the vessel and the complete withdrawal of the needle from the patient's body. The needle guard 30 is then advanced to its fullest extension as shown in FIG. 11. As it does so, the tapered proximal section 82 of the flash chamber base will spread the narrowed proximal portion 92 of the needle guard slot 36 until the narrowed portion 92 finally engages the aperture 74. At the fullest extension of the needle guard from the housing the engagement of the narrowed portion 92 in the aperture 74 will lock the needle guard in its protective position as shown in FIG. 11. The needle, housing and guard may then be set aside without concern for inadvertent injury to the user or others.

What is claimed is:
1. A catheter assembly comprising:
   a tubular needle housing having a distal end, a bottom patient facing surface and an open top;
   a hollow needle extending from the distal end of said needle housing;
   a tubular needle guard slideably located within said needle housing and including at its distal end means for engaging a catheter hub, said distal end having an aperture for passing said hollow needle therethrough; and
   means located partially on said needle housing and partially on said needle guard for locking said needle guard in an extended position relative to the distal end of said needle housing while maintaining said housing in the same orientation with respect to said needle guard throughout movement of said needle guard with respect to said housing; and
   a flash chamber located within said housing, wherein said flash chamber further includes a base for securing said flash chamber within said needle housing, and wherein said needle guard further includes a longitudinally extending slot which engages said flash chamber base as said needle guard slides within said needle housing.
2. The catheter assembly of claim 1, wherein said hollow needle extends from said flash chamber and the passageway of said hollow needle is in fluid communication with the interior of said flash chamber.
3. The catheter assembly of claim 2, wherein said flash chamber is located within said slideably mounted needle guard.
4. The catheter assembly of claim 1, wherein one longitudinal end of said flash chamber base is tapered to engage said needle guard slot during assembly of said needle guard and needle housing.
5. The catheter assembly of claim 1, wherein said needle housing further includes two lateral sides, wherein each lateral side includes a contoured finger grip.
6. The catheter assembly of claim 1, wherein said needle guard further includes an upward extending push tab located in the proximity of the distal end of said needle guard.
7. The catheter assembly of claim 6, wherein said needle guard further includes a plurality of projections located on the upper surface of said needle guard and accessible through said open top of said needle housing.
8. The catheter assembly of claim 1, wherein said means for locking includes a narrowed portion of said needle guard slot and an aperture located in said needle housing.
9. The catheter assembly of claim 1, wherein said needle guard comprises a longitudinal tubular section having a relatively large inner diameter and a distally mounted needle guard tip having a relatively small distal opening for passage about said hollow needle.
10. The catheter assembly of claim 1, further including a removable protective sheath which surrounds said needle prior to use of said assembly.
11. The catheter assembly of claim 10, wherein said sheath includes a longitudinally extending, generally planar bottom section.
12. The catheter assembly of claim 10, wherein said needle housing includes, at its distal end, means for engaging the proximal end of said protective sheath.

13. A catheter assembly comprising:
   a semi-tubular needle housing having an open top;
   a flash chamber located in the exterior of said needle housing and having a hollow needle extending from the distal end thereof;
   a tubular needle guard slideably located within said needle housing and including an aperture at its distal end for passage of said hollow needle therethrough;
   a catheter and catheter hub assembly suitable for mounting on the distal end of said needle guard; and
   means for locking said needle guard in an extended position relative to the distal end of said needle housing;
   wherein said flash chamber is located within said slideable tubular needle guard; and
   wherein said flash chamber further includes a base for securing said flash chamber within said needle housing, and wherein said needle guard further includes a longitudinally extending slot which engages said flash chamber base as said needle guard slides within said needle housing.

* * * * *